United States Patent [19]

Spahn et al.

[11] Patent Number: 5,111,807

[45] Date of Patent: May 12, 1992

[54] BACK BELT

[75] Inventors: James G. Spahn, Indianapolis; Steven P. Langley; Michael L. Jacobs, both of Martinsville, all of Ind.

[73] Assignee: EHOB Inc., Indianapolis, Ind.

[21] Appl. No.: 595,574

[22] Filed: Oct. 11, 1990

[51] Int. Cl.⁵ .................... A61F 5/02; A63H 33/08
[52] U.S. Cl. ................... 606/244; 128/DIG. 20; 128/99.1; 128/118.1; 24/90 HA
[58] Field of Search ............. 24/90 HA, 697.1, 693, 24/459; 128/68, 68.1, 78, 99.1, 112.1, 118.1, 384, DIG. 20, DIG. 15; 2/82, 338, 2; 446/107, 109, 120

[56] References Cited

U.S. PATENT DOCUMENTS

| | | |
|---|---|---|
| 1,646,590 | 10/1927 | Mildenberg |
| 2,554,337 | 5/1951 | Lampert |
| 3,052,236 | 9/1962 | Schrieber ............ 128/118.1 X |
| 3,071,133 | 1/1963 | Eisen |
| 3,521,623 | 7/1970 | Nichols et al. |
| 3,863,659 | 2/1975 | Gillis ............ 24/90 HA X |
| 3,987,580 | 10/1976 | Ausnit ............ 446/109 X |
| 4,135,503 | 1/1979 | Romano |
| 4,149,540 | 4/1979 | Hasslinger ............ 128/DIG. 15 X |
| 4,175,548 | 11/1979 | Henry |
| 4,178,922 | 12/1979 | Curlee |
| 4,178,923 | 12/1979 | Curlee |
| 4,552,135 | 11/1985 | Racz et al. |
| 4,622,957 | 11/1986 | Curlee |
| 4,682,587 | 7/1987 | Curlee |
| 4,682,588 | 7/1987 | Curlee |
| 4,836,194 | 6/1989 | Sebastian et al. ............ 128/78 |
| 4,864,698 | 9/1989 | Brame ............ 128/DIG. 15 X |
| 4,988,322 | 1/1991 | Knudsen ............ 446/120 |
| 4,993,409 | 2/1991 | Grim ............ 128/78 |

FOREIGN PATENT DOCUMENTS

| | | | |
|---|---|---|---|
| 234720 | 10/1959 | Australia ............ 24/693 |
| 1461408 | 12/1966 | France |
| 163116 | 10/1969 | Netherlands |
| 117148 | 7/1918 | United Kingdom |
| 985591 | 3/1965 | United Kingdom |

Primary Examiner—Richard J. Apley
Assistant Examiner—Linda C. M. Dvorak
Attorney, Agent, or Firm—Woodard, Emhardt, Naughton, Moriarty & McNett

[57] ABSTRACT

A back belt comprising a continuous, non-baffled, pressurizable air chamber having a top edge, a bottom edge, and a pair of opposing ends defining the periphery thereof; cushioning rims along the top and bottom edges of the air chamber; symmetrical contouring notches along the top and bottom edges of the air chamber and along the cushioning rims; belt means connected to the ends of the air chamber; valve means on the air chamber operable to allow presurization of the air chamber to a desired internal air pressure; and supportive wall means overlaying the air chamber to provide stability and durability to the air chamber, and connected to the belt means and to the air chamber at the ends of the air chamber; and a novel connector permanently couples the materials from which the air chamber and belt straps for the air chamber of the preferred embodiment of the invention are constructed, providing a stability to the joinder of these materials not obtainable by known sewing means, thereby enhancing the durability of the joinder.

9 Claims, 4 Drawing Sheets

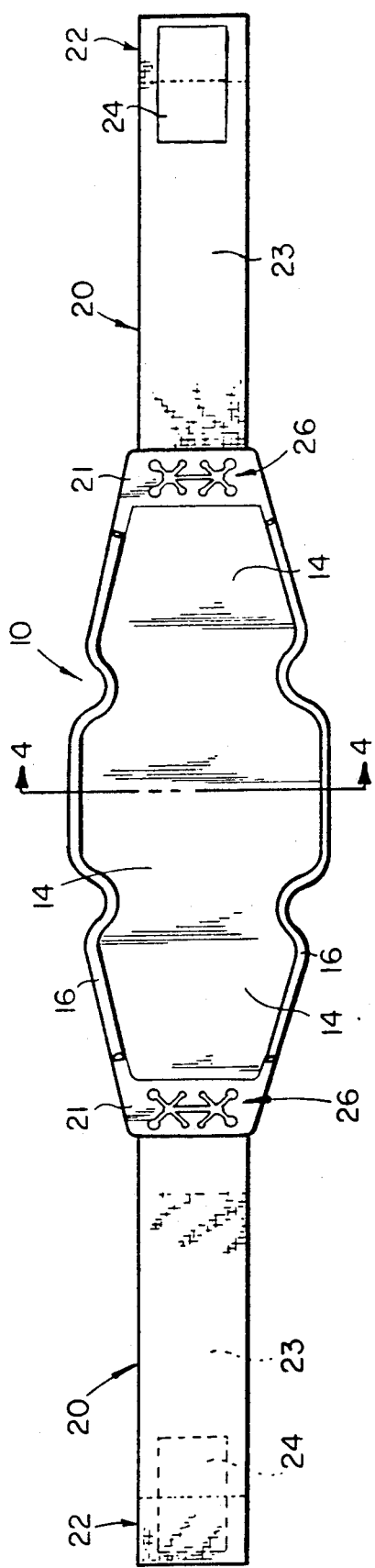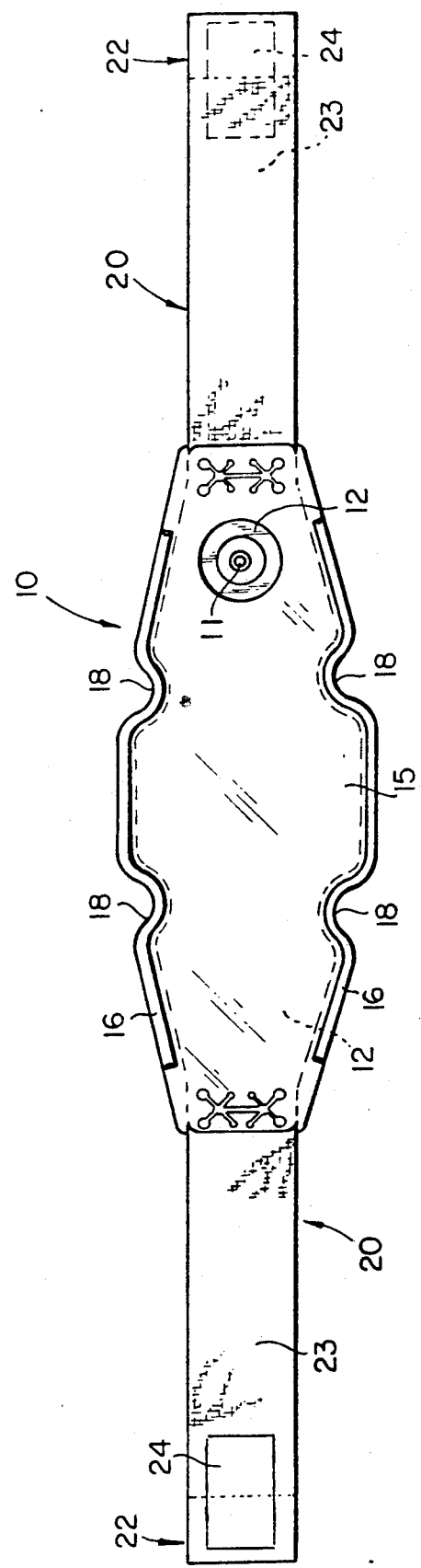

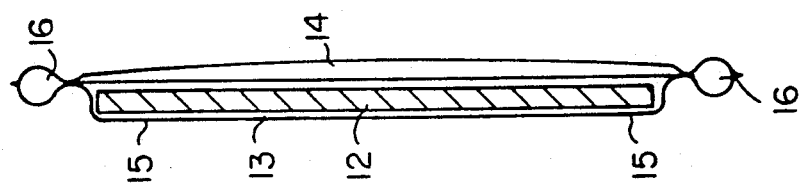
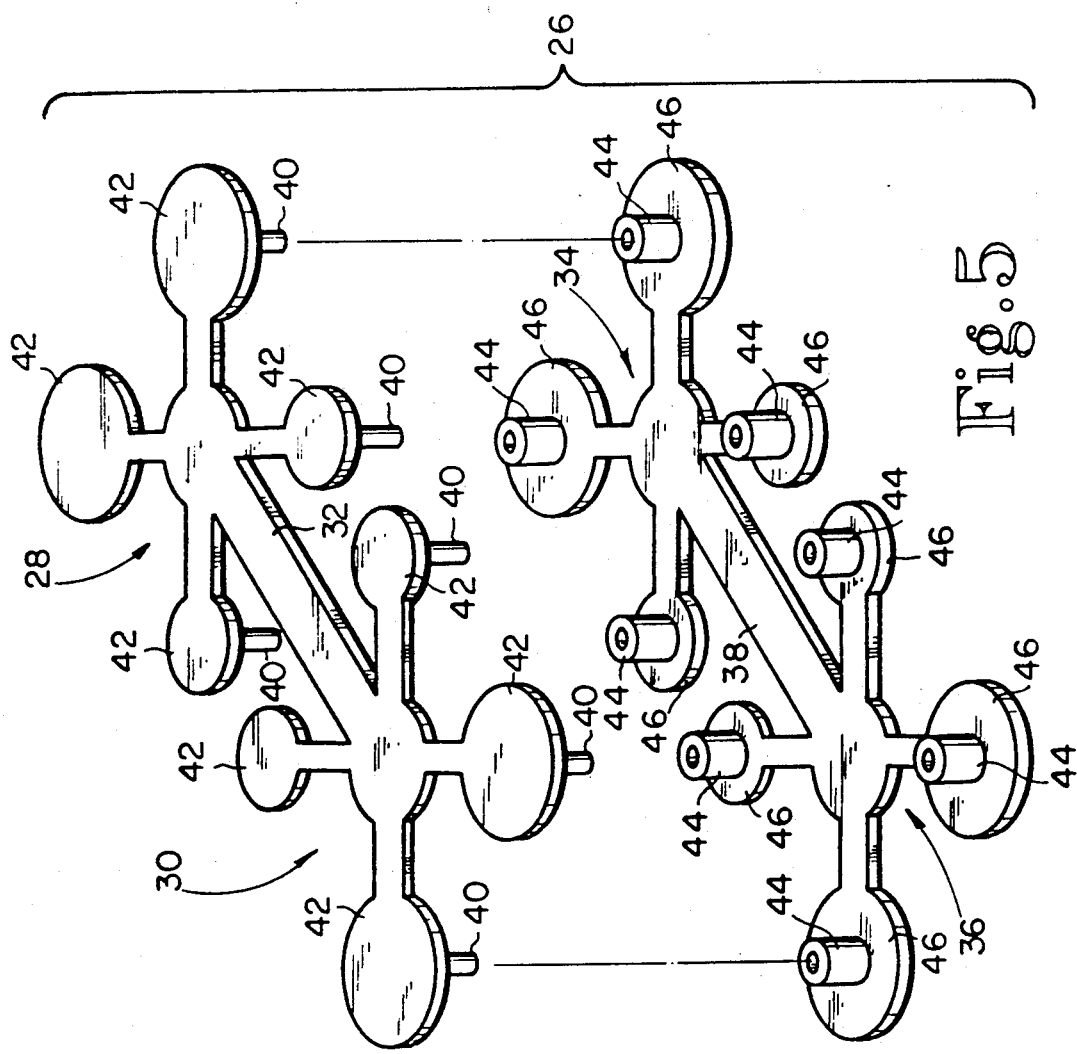

BACK BELT

The present invention relates generally to the field of air inflatable appliances for therapeutic use, and more particularly is concerned with an air inflatable lower back belt that assists the wearer in maintaining a proper posture in a variety of torso positions to aid in the prevention or alleviation of lower back pain.

SUMMARY OF THE INVENTION

The back belt of the present invention exerts an equalized pressure on the lower back area of the wearer through the use of a continuous, non-baffled, pressurizable air chamber that tends to massage and relax the lower back muscles as the torso moves. Two permanently air-pressurized cushioning rims located along the lengths of the top and bottom edges of the air chamber enhance the ability of the air chamber to contour to the lower back area of the wearer, and create comfort buffers above and below the air chamber. Symmetrical contouring notches located along the top and bottom edges of the air chamber and cushioning rims promote ease of movement of the back belt about its longitudinal axis, and thus ease of movement of the wearer.

A novel connector permanently couples the materials from which the air chamber and belt straps for the air chamber of the preferred embodiment of the invention are constructed, providing a stability to the joinder of these materials not obtainable by known sewing means, thereby enhancing the durability of the joinder.

At the loose ends of the belt straps for the air chamber of the preferred embodiment are finger loops that allow for a novel over/under two-handed closure and tensioning of the belt straps around the girth of the wearer, utilizing conventional loop and hook fasteners.

One embodiment of the present invention is a back belt comprising a continuous, non-baffled, pressurizable air chamber having a top edge, a bottom edge, and a pair of opposing ends defining the periphery thereof; cushioning rims along the top and bottom edges of the air chamber; symmetrical contouring notches along the top and bottom edges of the air chamber and along the cushioning rims; belt means connected to the ends of the air chamber; and valve means on the air chamber operable to allow pressurization of the air chamber to a desired internal air pressure.

Another embodiment of the present invention is a back belt comprising a continuous, non-baffled, pressurizable air chamber having a top edge, a bottom edge, and a pair of opposing ends defining the periphery thereof; cushioning rims along the top and bottom edges of the air chamber; symmetrical contouring notches along the top and bottom edges of the air chamber and along the cushioning rims; belt means connected to the ends of the air chamber; valve means on the air chamber operable to allow pressurization of the air chamber to a desired internal air pressure; and supportive wall means overlaying the air chamber to provide stability and durability to the air chamber, and connected to the belt means and to the air chamber at the ends of the air chamber.

Another embodiment of the present invention is a connector for coupling a plurality of materials together, comprising a plurality of planar X-shaped male members joined at their midpoints by first interconnecting members running between the midpoints of the X-shaped male members; a mirror image plurality of planar X-shaped female members joined at their midpoints by second interconnecting members running between the midpoints of the X-shaped female members; a stake at the outer most point of each of the X shaped male members disposed at a right angle to the plane of the X-shaped male member and downwardly from a first head member attached in planar relationship to the outer most points of each of the X-shaped male members; a receptor at the outer most point of each X-shaped female members shaped and sized to matingly receive corresponding stakes of the X-shaped male members, the receptors being each disposed upwardly and equidistance from a second head member attached in planar relationship to the outer-most points of the X shaped female members, the measure of the upward disposition of the receptors being equal to the combined thicknesses of the materials to be joined by the connector between the X-shaped male and female members.

It is an object of the present invention to provide a back belt that exerts equalized pressure on the lower back area with a continuous, non-baffled, pressurizable air chamber that massages and relaxes the lower back muscles as the wearer's torso moves.

It is a further object of the present invention to provide a low pressure, low profile, air inflatable back belt that will maintain capillary blood flow in the lower back region when in use.

It is a further object of the present invention to provide a back belt that promotes ease of movement by not restricting the amount or degree of torso movement.

It is a further object of the present invention to provide a novel connector that permanently couples dissimilar materials with a stability not obtainable by conventional sewing means, thereby enhancing the durability of the joinder.

Related objects and advantages of the present invention will be apparent from the following descriptions.

BRIEF DESCRIPTION OF THE DRAWINGS

FIG. 1 is a front elevational view of the preferred embodiment of the back belt of the present invention.

FIG. 2 is a rear elevational view of the back belt of FIG. 1.

FIG. 4 is an enlarged cross-sectional view of the back belt of FIG. 1 taken along line 4—4 in the direction of the arrows.

FIG. 5 is a perspective and exploded view of the novel connector utilized in the construction of the preferred embodiment of the back belt of FIG. 1.

DESCRIPTION OF THE PREFERRED EMBODIMENTS

Figure 3:
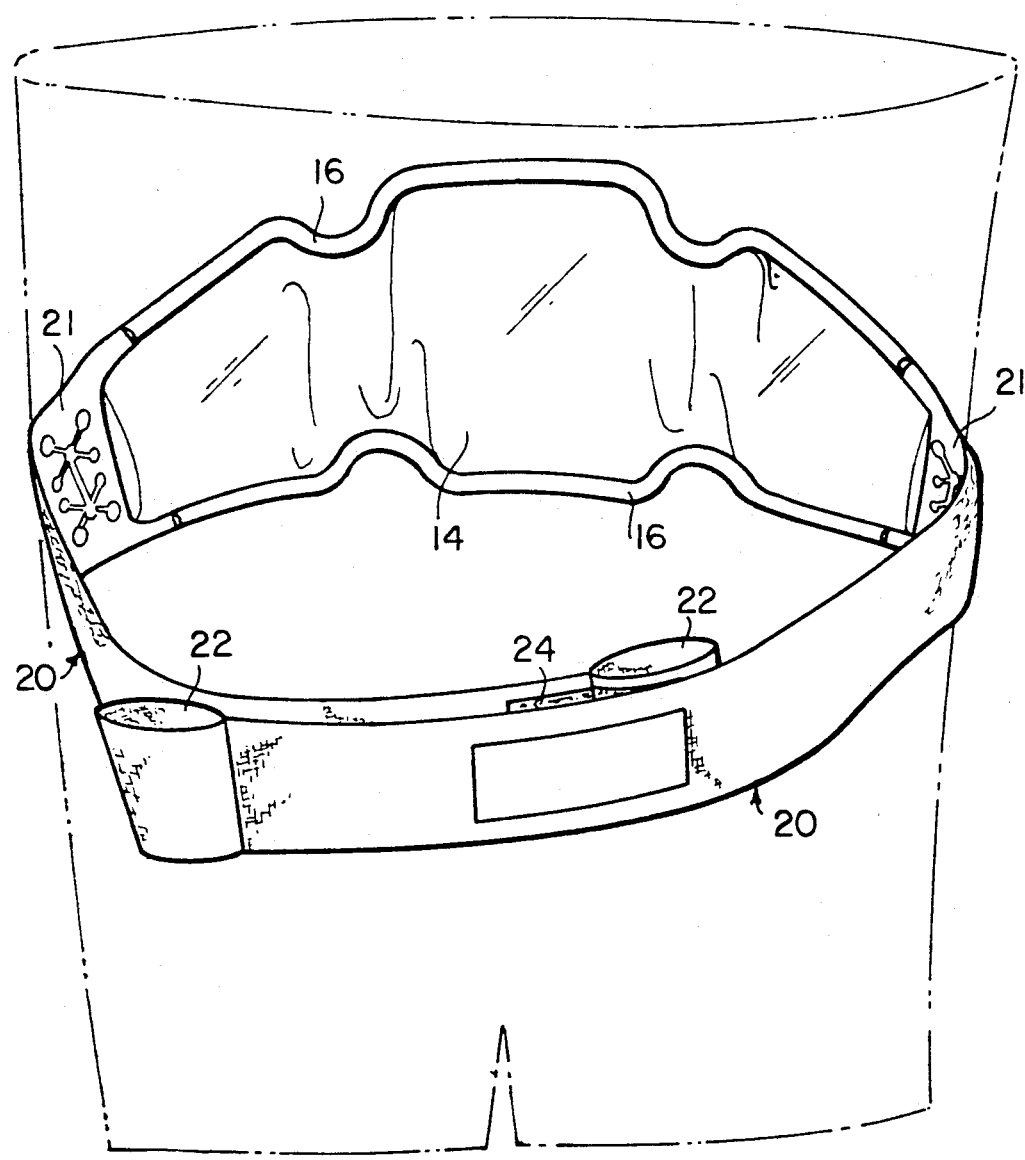
FIG. 3 is a perspective view of the back belt of FIG. 1 in place around the girth of a wearer.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to the drawings, there is shown in the FIGS. a preferred embodiment of the back belt 10 of the present invention. Back belt 10 is composed of a single, continuous, non-baffled air chamber 14 constructed from a pair of plastic sheets that have been peripherally joined together by conventional plastic welding techniques to form a pressurizable air chamber 14 of desired peripheral dimensions.

Along the top and bottom edges of air chamber 14 are permanently air-pressurized cushioning rims 16 that enhance the ability of air chamber 14 to contour to the lower back area of a wearer while creating soft, comfort buffers for the wearer's lower back during torso movement. In the preferred embodiment, cushioning rims 16 are also formed from a pair of plastic sheets that have been peripherally joined together by conventional plastic welding techniques to form air-pressurizable cushioning rims 16 of the desired peripheral dimensions along the top and bottom edges of air chamber 14. In the preferred embodiment, cushioning rims 16 are permanently air pressurized and sealed at the time of manufacture.

Back belt 10 of the preferred embodiment has a multi-layered construction for stability and durability. Referring to FIGS. 2 and 4, in the preferred embodiment a die cut leather layer 12 is encased within a non-air bearing chamber 13 formed at the rear of back belt 10 (FIGS. 2 and 4) by a third sheet of plastic material 15 that has been conventionally heat sealed about the peripheral heat seal that formed air chamber 14. In the preferred embodiment, the leather layer 12 is die cut to overlay air chamber 14 with the peripheral edges of leather layer 12 lying approximately an eighth inch inside the peripheral edges of air chamber 14. The leather layer 12 thus creates a supportive wall behind air chamber 14 for stability and durability.

Referring to FIG. 2, there is a conventional recessive air valve 11 sealed into the rear of air chamber 14 that is accessible from the rear of back belt 10 through an appropriately sized opening provided in the leather layer 12 and the plastic sheet material 15 that forms the non-air bearing chamber 13 encasing the leather layer 12 in the preferred embodiment. Air valve 11 allows the air within air chamber 14 to be pressurized to any desired level.

As described, air chamber 14 in conjunction with the stability provided by leather layer 12 of the preferred embodiment allows a uniform pressure to be applied to the lower back area of the wearer (FIG. 3). The single, non-baffled air chamber 14 allows for maximum surface contact of air chamber 14 with the lower back region of the torso for pressure relief at the critical muscular skeletal support area of the lower back region. It has been determined that the fluctuation in the volume of a single, non-baffled air chamber 14 that occurs as the wearer's torso moves creates a corresponding massaging action along the lower back area covered by air chamber 14 that tends to relax lower back muscles.

Symmetrical contouring notches 18 (FIG. 2) formed along the top and bottom edges of air chamber 14 and cushioning rims 16 allow for air circulation between the back belt 10 and the torso of the wearer, and also provide needed flexibility along these edges of air chamber 14 and cushioning rims 16 to comfortably accommodate the wearer's torso movements that would tend to twist back belt 10 along its longitudinal axis.

In the preferred embodiment, belt straps 20 are secured to each end of the air chamber 14 at tabs 21, where the materials that have formed air chamber 14, leather layer 12, and non-pressurized chamber 13 have been overlapped to form tabs 21. In the preferred embodiment, belt straps 20 are made of a laminated nylon material suitable for the attachment of conventional loop 23 and hook 24 fasteners thereto (FIGS. 1 and 2), such as VELCRO ® brand loop and hook fasteners. In the Preferred embodiment, nylon strap material was selected for its strength, flexibility, soft and comfortable feel, and its suitability as a low profile abdominal support.

Figure 6:
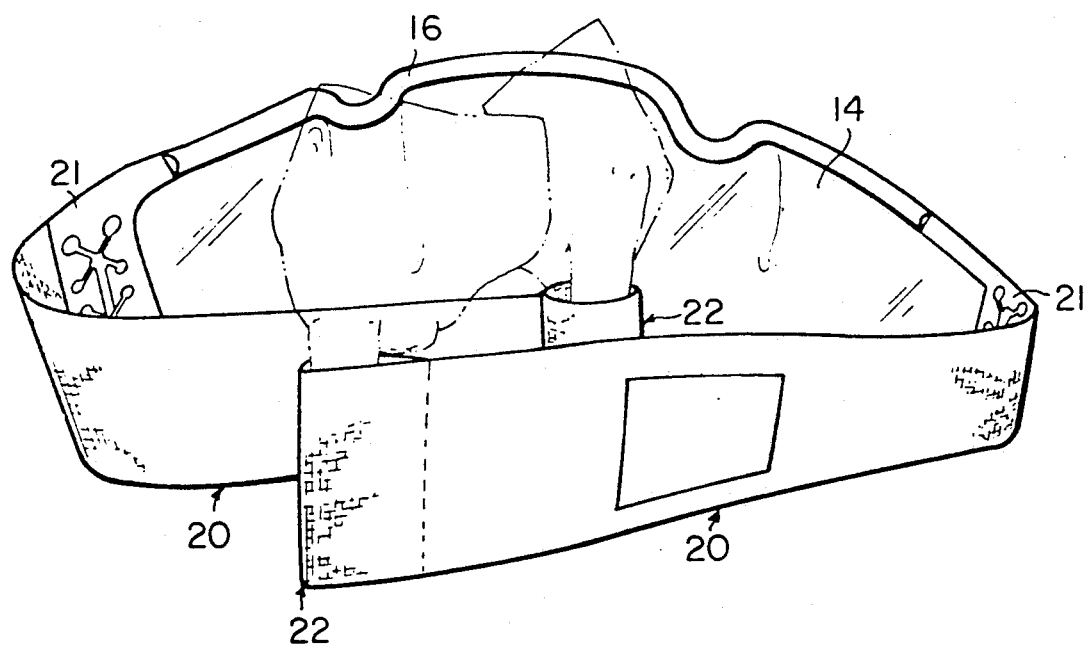
FIG. 6 is a perspective view of the back belt of FIG. 1 being put in place utilizing the finger loops of the preferred embodiment and showing the novel over/under two-handed closure and tensioning of the belt straps of the preferred embodiment of the back belt of FIG. 1.

Belt straps 20 are provided with finger tensioning loops 22 on each loose end that are formed in the preferred embodiment by doubling back the loose end of each belt strap 20 and fastening the loose end to the corresponding belt strap 20. The hooks 24 of the loop and hook fasteners are attached on each end of the belt straps 20 underneath the finger tensioning loops 22 to allow a wide range of girth adjustability. Finger tensioning loops 22 then allow for a novel and easy over-/under two-handed closure of the belt strap (FIG. 6).

As described, belt straps 20 of the preferred embodiment provide a quick, one-handed peel away release for safety reasons. However, the loop and hooks fasteners maintain good shear strength when the back belt 10 is worn for long periods of time.

Belt straps 20 are secured to air chamber 14 and leather layer 12 at tabs 21 by a novel connector 26 that is designed to permanently couple two or more materials, the joinder of which would otherwise be unduly weakened by conventional sewing techniques, for example. In the preferred embodiment of back belt 10, sewing of the nylon belt straps 20 to the leather layer 12 was found to unacceptably weaken the leather layer 12 where sewn, and thus the joinder of the belt straps 20 to the air chamber 14 and leather layer 12 was weakened unacceptably.

Referring now to FIG. 5, connector 26 is designed to permanently couple two materials in a manner that is superior to conventional sewing, for example. Connector 26 of the preferred embodiment consists of a pair of planar X-shaped male members 28 and 30 that are joined at their midpoints by a co-planar interconnecting member 32 running between the midpoints of said X-shaped male members; and a mirror image pair of planar X-shaped female members 34 and 36 that are joined at their midpoints by a co-planar interconnecting member 38 also running between the midpoints of said X-shaped female members.

At the outer most points of the X-shaped male members 28 and 30 are stakes 40, each disposed at a right angle to the plane of said X-shaped male members and downwardly from head members 42 that are attached in planar relationship to the outer-most points of the X-shaped male members 28 and 30.

At the outer most points of the X-shaped female members 34 and 36 are receptors 44 shaped and sized to matingly receive corresponding stakes 40 of said X-shaped male members, said receptors being disposed upwardly and equidistance from head members 46 that are attached in planar relationship to the outer-most points of the X-shaped female members 34 and 36. The measure of the upward disposition of receptors 44 will be the combined thicknesses of the materials to be joined.

Through holes are provided in the materials to be joined by connector 26 to accommodate the shape and dimensions of the receptors 44 of the X-shaped female members. Stakes 40 are then mated with corresponding receptors 44 such that the head members 42 contact receptors 44, with the materials to be joined disposed between X-shaped male members 28 and 30 and X-shaped female members 34 and 36. Stakes 40 are then permanently affixed within receptors 44 by conventional ultrasonic and/or heat staking technology in the preferred embodiment.

Connector 26, thus fastened, has a very low profile, and has provided a permanent coupling of two or more joined materials with fewer and more widely dispersed through holes in the materials so joined than had they been sewn together by conventional means.

In a preferred embodiment, connector 26 is made from a lightweight plastic material suitable for fixing with conventional ultrasonic and/or heat staking technology.

While the preferred embodiment of connector 26 described above has only a pair of X-shaped members, it is to be understood that multiple X-shaped members could be interconnected together in the manner taught to accommodate any width of materials to be joined, or the disposition of multiple X-shaped members within a plane could be arranged to accommodate a wide variety of joint shapes.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A back belt, comprising:
   a continuous, non-baffled, pressurizable air chamber having a top edge, a bottom edge, and a pair of opposing ends defining the periphery thereof;
   cushioning rims along the top and bottom edges of said air chamber;
   symmetrical contouring notches along the top and bottom edges of said air chamber and along said cushioning rims; belt means connected to the ends of said air chamber; and valve means on said air chamber operable to allow pressurization of said air chamber to a desired internal air pressure.

2. The back belt of claim 1 and further comprising:
   supportive wall means overlaying said air chamber to provide stability and durability to said air chamber, and connected to said belt means and to said air chamber at the ends of said air chamber.

3. The back belt of claim 1 wherein:
   said air cushion and cushioning rims each include a pair of plastic sheets peripherally joined together to form an air pressurizable chamber.

4. The back belt of claim 3 wherein:
   said cushioning rims are air pressurized and permanently sealed.

5. The back belt of claim 2 wherein:
   said belt means include a pair of belt straps each provided with loop and hook fasteners and finger tensioning means at the loose ends thereof to permit an over/under two-handed closure of said straps about the girth of a wearer, utilizing said finger tensioning means and said loop and hook fasteners.

6. The back belt of claim 1 wherein:
   said belt means includes a connector comprising a plurality of planar X-shaped male members joined at their midpoints by first interconnecting members running between the midpoints of said X-shaped male members; a mirror image plurality of planar X-shaped female members joined at their midpoints by second interconnecting members running between the midpoints of said X-shaped female members; a stake at the outer most point of each of said X-shaped male members disposed at a right angle to the plane of said X-shaped male member and downwardly from a first head member attached in planar relationship to the outer most points of each of said X-shaped male members; a receptor at the outer most point of each X-shaped female members shaped and sized to matingly receive corresponding stakes of said X-shaped male members, said receptors being each disposed upwardly and equidistance from a second head member attached in planar relationship to the outer-most points of said X-shaped female members, the measure of said upward disposition of said receptors being equal to the combined thicknesses of the materials to be joined by said connector between said X-shaped male and female members.

7. The back belt of claim 6 wherein:
   said connector is made from a plastic material suitable for fixing with conventional ultrasonic or heat staking technology.

8. A connector for coupling a plurality of materials together, comprising:
   a plurality of planar X-shaped male members joined at their midpoints by first interconnecting members running between the midpoints of said X-shaped male members; a mirror image plurality of planar X-shaped female members joined at their midpoints by second interconnecting members running between the midpoints of said X-shaped female members; a stake at the outer most point of each of said X-shaped male members disposed at a right angle to the plane of said X-shaped male member and downwardly from a first head member attached in planar relationship to the outer most points of each of said X-shaped male members; a receptor at the outer most point of each X-shaped female members shaped and sized to matingly receive corresponding stakes of said X-shaped male members, said receptors being each disposed upwardly and equidistance from a second head member attached in planar relationship to the outer-most points of said X-shaped female members, the measure of said upward disposition of said receptors being equal to the combined thicknesses of the materials to be joined by said connector between said X-shaped male and female members.

9. The back belt of claim 8 wherein:
   said connector is made from a plastic material suitable for fixing with conventional ultrasonic or heat staking technology.

* * * * *

UNITED STATES PATENT AND TRADEMARK OFFICE
CERTIFICATE OF CORRECTION

PATENT NO. : 5,111,807
DATED : May 12, 1992
INVENTOR(S) : James G. Spahn et al.

It is certified that error appears in the above-identified patent and that said Letters Patent is hereby corrected as shown below:

In column 5, line 58, change the word "cushion" to -- chamber --.

Signed and Sealed this

Twelfth Day of July, 1994

Attest:

BRUCE LEHMAN

*Attesting Officer*  *Commissioner of Patents and Trademarks*